United States Patent [19]
Gerstel

[11] Patent Number: 4,854,181
[45] Date of Patent: Aug. 8, 1989

[54] SAMPLE INJECTION OR EXTRACTION HEAD FOR GASEOUS OR LIQUID FLUIDS

[76] Inventor: Eberhard Gerstel, Heerstr. 4, D-4330 Mülheim a.d. Ruhr 14, Fed. Rep. of Germany

[21] Appl. No.: 158,934

[22] Filed: Feb. 22, 1988

[30] Foreign Application Priority Data

Nov. 28, 1987 [DE] Fed. Rep. of Germany ... 8715782[U]

[51] Int. Cl.$^4$ .......................... G01N 1/00; G01N 30/16
[52] U.S. Cl. ................................ 73/863.86; 73/864.87
[58] Field of Search ........... 73/863.81, 863.82, 863.83, 73/863.84, 863.85, 863.86, 864.21, 864.73, 864.74, 864.81, 864.83, 864.84, 864.85, 864.86, 864.87; 55/386; 210/198.2, 656

[56] References Cited

U.S. PATENT DOCUMENTS

| | | | |
|---|---|---|---|
| 3,201,994 | 8/1965 | Adams | 73/864.74 |
| 3,566,698 | 3/1971 | Sheppard | 73/864.85 |
| 3,858,449 | 1/1975 | Singer | 73/863.86 |
| 3,930,413 | 1/1976 | Laird et al. | 73/863.85 |
| 4,580,453 | 4/1986 | Taylor | 73/863.86 |

FOREIGN PATENT DOCUMENTS 3400458  4/1987  Fed. Rep. of Germany .

*Primary Examiner*—Stewart J. Levy
*Assistant Examiner*—Robert R. Raevis
*Attorney, Agent, or Firm*—Frishauf, Holtz, Goodman & Woodward

[57] ABSTRACT

A sample injection or extraction head for gaseous or liquid fluids, especially for use in gas chromatography. An inner bore of the head is in alignment with a passage of an introduction opening for receiving a syringe needle. The introduction opening is connected with the inner bore via a seal so that a syringe needle which has been inserted through the introduction opening into the inner bore is sealed against the exterior via the seal. An inlet valve is provided having a valve body which is sealingly spring biased against the inner bore and is displaceable by the introduction of a syringe needle for opening the valve against the spring bias, such displacement taking place at an angle between the axis of the inner bore and the axis of the valve within the range of more than 90° up to less than 180°. A cylindrical guide for the valve body ends in a recess of the head. The recess extends across the inner bore and provides an annular sealing surface. A substantially cylindrical protrusion member supports a sealing ring which, in the closed position of the valve, is in sealing engagement with the sealing surface. Thus, the protrusion member extends into the recess so that upon the introduction of a syringe needle the needle tip first impinges onto the front face of the protrusion member and displaces the valve body together with the sealing ring out of the recess.

9 Claims, 2 Drawing Sheets

SAMPLE INJECTION OR EXTRACTION HEAD FOR GASEOUS OR LIQUID FLUIDS

BACKGROUND OF THE INVENTION

The invention concerns a sample injection and extraction head, respectively, for gaseous or liquid fluids especially for the use in gas chromatography, more especially in capillary chromatography. Sample injection heads are especially used in septum-free cold sample injection, preferably in oncolumn mode, according to which a sample to be analyzed is injected into the chromatographic system.

From the German Patent No. 3.400.458 a septum-free sample injection head for the use in capillary gas chromatography is known which is provided with an inlet valve having a valve body being spring biased against a sealing ring. The valve body is a ball which upon insertion of a syringe needle is obliquely thrusted away against the spring bias and the syringe needle is introduced into the injection head through the sealing ring. However, the introduction through the sealing ring risks to damage the sealing ring. Furthermore, the sealing ring comes out of round by clamping it between the valve housing and the injection head so that the pressing force of the ball-like valve body has to be relatively great to ensure a continuous line contact of the ball-like valve body and the sealing ring. This makes the valve difficult to actuate. The adjustment of the ball and the valve housing which is to be provided with a passage for the syringe needle is also difficult to manage and a corresponding machining is necessary.

SUMMARY OF THE INVENTION

It is an object of the present invention to provide a sample injection head for gaseous or liquid fluids preventing a damaging of the sealing of the inlet valve during the introduction of a syringe needle.

It is a further object of the present invention to provide a sample injection head for gaseous or liquid fluids which is easy to actuate.

It is still a further object of the present invention to provide a sample injection head for gaseous or liquid fluids which can easily be mounted together.

Additionally, it is an object of the invention to provide a head which can be used for sample extraction.

According to the invention a sample injection or extraction head for gaseous or liquid fluids is provided, comprising an inner bore in alignment with a passage of an introduction means for a syringe needle, said introduction means being connected with the head via a sealing means so that a syringe needle for injecting or extracting a sample and being introduced through said introduction means into the head is sealed against the exterior via said sealing means; further comprising an inlet valve means with a valve body which is sealingly spring biased against said inner bore and displaceable by the introduction of a syringe needle for opening said valve means against said spring bias, said displacement taking place within an angle of more than 90° up to less than 180°, especially between 120° and 150° (in view from the introduction side of said syringe needle). A cylindrical guide means is provided for the valve body, said guide means ending in a recess means of said head which recess means extends over the area of said inner bore and provides an annular sealing surface means. The valve body has a substantially cylindrical protrusion member supporting a sealing ring which in the closed position of said valve means is in sealing engagement with said sealing surface means, wherein said protrusion member extends into said recess means so that upon the introduction of a syringe needle its tip first impinges onto the front face of said protrusion member under the above mentioned angle and displaces said valve body together with said sealing ring out of said recess means so that during the further introduction of the syringe needle said sealing ring is protected against damage by said protrusion member. The sealing ring is only clamped between the annular sealing surface means and the valve body so that at least a continuous line sealing contact is ensured. The necessary sealing force is relatively low.

The head according to the invention is simple with respect to its construction and assembly. Since no special precise mechanical work is necessary, there is no more the need to fabricate the head out of metal, especially stainless steel, instead the head and the essential parts of the inlet valve may be moulded from plastic material. No special adjustment or machining is necessary.

The protrusion member of the valve body extending into the recess means crossing the inner bore of the head can be provided with a relatively large play or clearance with respect to the recess means so that it does not clamp within its housing during its removal so that it can be easily removed. But it is also possible to provide the valve body with a threaded bore or the like so that it can be removed by using a corresponding tool.

It is advantageous when the head is also the housing for the inlet valve and is provided with a bore used as guiding means for the valve body. This bore may be closed to the exterior by a plug supporting the biasing spring of the valve body.

This and other objects and embodiments of the present invention will become more apparent during the course of the following description and appended claims.

DETAILED DESCRIPTION OF THE PREFERRED EMBODIMENTS

The present invention will hereunder be described in further detail with respect to the attached drawings.

Figure 1:
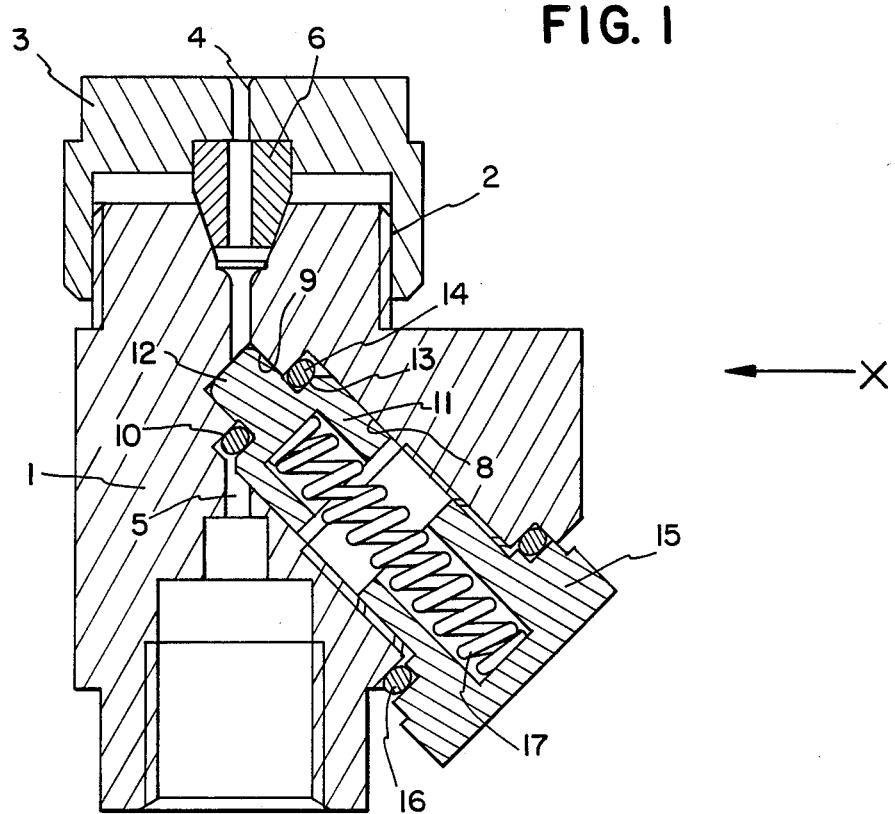
FIG. 1 shows a sectional view of a septum-free sample injection head for capillary gas chromatography.
Figure 2:
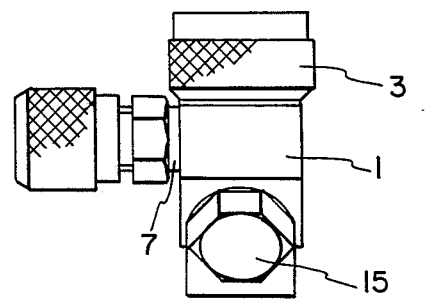
FIG. 2 shows a reduced scale a view according to arrow "X" from FIG. 1.

In FIGS. 1 and 2, the sample injection head is denominated by reference number 1 and provided with a threaded section 2 onto which an introduction cap 3 for introducing a syringe needle is screwed. The introduction cap 3 has a bore 4 which is in alignment with a bore 5 of head 1. The bore 4 serves as a guide means for syringe needles. Between the introduction cap 3 and the head 1 a screw tightened sealing body 6 is arranged which is provided with a passage connecting the bores 4 and 5. Syringe needles pass through said passage of the sealing body 6 during their introduction into head 1. During the passage of a syringe needle through the sealing body 6 the latter sealingly contacts the syringe needle so that the bore 5 is sealed against the exterior.

At the end opposite to the introduction cap 3, the bore 5 is provided with a stepped bore which is partly threaded to be engageable with an end section of a sample trapping chamber or a bottle or the like. According to the provided range of use the head 1 may have a gas connection 7 for instance for carrier gas.

The head 1 has a bore 8 having an angle of 135° with respect to the axis of bore 5 (seen from above). The outer end section of the bore 8 is threaded. At the opposite end of the bore 8 a cylindrical recess 9 which is coaxially arranged to the bore 8 is provided. The recess 9 extends over the region of the bore 5. An annular sealing surface 10 which extends vertically to the axis of the bore 8 is provided between the bore 8 and the recess 9.

The bore 8 serves as a guide for a circular-cylindrical valve body 11 having a coaxial protrusion 12 of reduced diameter so that there exists an annular surface 13 of the valve body 11 which faces to the sealing surface 10 in parallel relationship thereto. Adjacent to the annular surface 13 the protrusion 12 supports a sealing ring 14 which is held by an annular groove and moveable together with the valve body 11 within the bore 8. The bore 8 is closed to the exterior by a screw-like plug 15. Between the plug 15 and the head 1 a seal 16 is provided. The plug 15 takes up a compression spring 17 biasing the valve body 11 in the direction to the bore 5. In the closed position of the inlet valve the sealing ring 14 is pressed between the surfaces 10 and 13 by the spring 17 to seal the bore 5 against the exterior. The front face of the protrusion 12 is in contact with the bottom of the recess 9 or with small distance thereto so that the front face of the protrusion 12 substantially covers the mouth area of the bore 5 into the recess 9 from the side of the introduction cap 3.

In the case of introducing a syringe needle its tip impinges onto the front face of the protrusion 12, which front face extends obliquely to the bore 5, and presses the valve body 11 against the force of the biasing spring 17 within the guide bore 8 out of the region of the bore 5. At the same time this displacement of the valve body 11 secures that the sealing ring 14 is moved out of its engagement with the sealing surface 10 and out of the region of the bore 5. The sealing function is at this time taken over by the sealing body 6.

The gas connection 7 is connected with the bore 5 beneath the annular surface 13 which also serves as sealing surface. The gas connection 7 is for instance used for the supply of carrier gas or for purging.

The head 1, the valve body 11 and the plug 15 as well as the introductory cap 3 can be out of plastics, for instance injection molded. A special adjustment is not necessary since the allowable tolerances are not critical.

Figure 3:
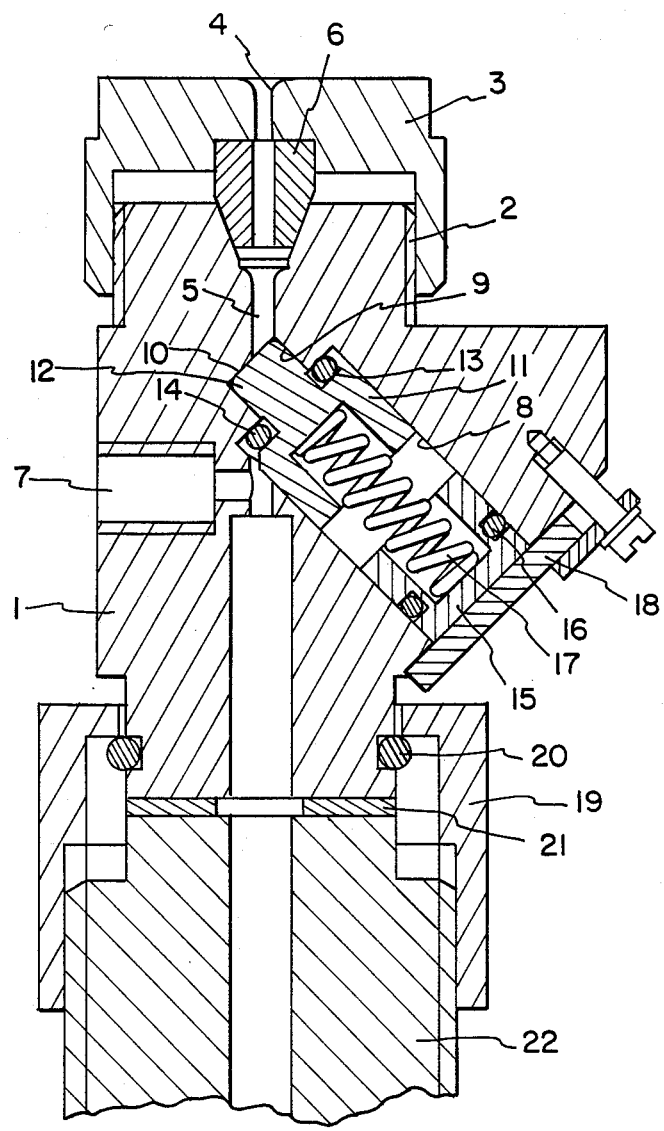
FIG. 3 shows a sectional view of a further embodiment of a sample injection means.

The bore 8 of the embodiment shown in FIG. 3 is not threaded and, furthermore, the plug 15 together with the sealing ring 16 which is supported by the plug is inserted into the bore 8 and held there by a plate 18 screwed with the head 1.

Additionally, a screw cap 19 is provided at the lower end of the head 1 which is held by a snap ring 20. In this case, the head 1 is screwed onto a member 22, for instance a precolumn, a container or the like, with a flat seal 21 therebetween.

Although the above discussed embodiments have been described in connectio with the sample introduction in capillary gas chromatorgraphy it is well understood that the head according to this invention, besides its preferred use as sample injection head of a cold injection system for gas chromatography, may also be used as sample extraction head, for instance to extract a sample from a container like a bottle or trap as for instance used in gas chromatography. Furthermore, the heads may be used in connection with the injection for extraction of gas or liquid.

While preferred embodiments have been shown and described, various modifications and substitutions may be made thereto without departing from spirit and scope of the invention. Accordingly, it is to be understood that the present invention has been described by way of illustration and not limitation.

I claim:

1. A head used for gaseous or liquid fluids to perform at least one of sample injection and extraction, comprising:

an inner bore within the head sized to accommodate a syringe needle thereinto;

an inlet valve means having a closed position for blocking the inner bore and including a substantially cylindrical valve body which is sealingly spring biased toward said inner bore and having a protrusion member extending into recess means of said head and being displaceable by a syringe needle being inserted into said inner bore for moving said valve means against said spring bias in a direction along the valve body axis which forms an angle in the range of greater than 90° up to less than 180° with the axis of the inner bore through which the syringe needle passes toward said recess means;

a cylindrical guide means within the head for said valve body, said guide means ending in said recess means of said head, which recess means extends across and in communication with said inner bore and provides an annular sealing surface means; and said cylindrical protrusion member of the valve body supporting a sealing ring which, in the closed position of said valve means, is in sealing engagement with said sealing surface means;

wherein said protrusion member extends into said recess means so that upon the introduction of a syringe needle its tip first impinges onto the front face of said protrusion member and displaces said valve body together with said sealing ring out of said recess means.

2. The head of claim 1, wherein the head is made of plastic material.

3. The head of claim 2, wherein the valve body is of plastic mateiral.

4. The head of claim 1, wherein the valve is made of plastic material.

5. The head of claim 1, wherein the protrusion member has clearance to said recess means.

6. The head of claim 1, wherein said guide means is threaded at the end portion adjacent to the exterior and closed by a plug means supporting a spring biasing said valve body.

7. The head of claim 1, wherein said guide means is closed to the exterior by a plug being supported by a plate secured to the inlet valve means.

8. The head of claim 1, wherein said guide means is a bore within the head.

9. The head of claim 1, wherein said head further comprises an introduction means having an opening to the exterior of the head in alignment with the inner bore and sized to accommodate a syringe needle therein; a sealing means between the introduction means and the inner bore for sealing the head from the exterior when a syringe needle is passed through the introduction means and the sealing means into the inner bore.

* * * * *